(12) United States Patent
Armstrong et al.

(10) Patent No.: US 10,117,690 B2
(45) Date of Patent: Nov. 6, 2018

(54) SPINAL IMPLANT SYSTEM AND METHOD

(71) Applicant: Warsaw Orthopedic, Inc., Warsaw, IN (US)

(72) Inventors: William D. Armstrong, Memphis, TN (US); Stanley T. Palmatier, Olive Branch, MS (US); Virginia Leigh Richardson, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 408 days.

(21) Appl. No.: 14/835,158

(22) Filed: Aug. 25, 2015

(65) Prior Publication Data

US 2016/0067051 A1 Mar. 10, 2016

Related U.S. Application Data

(60) Provisional application No. 62/047,966, filed on Sep. 9, 2014.

(51) Int. Cl.
*A61F 2/44* (2006.01)
*A61B 17/80* (2006.01)
*A61B 17/70* (2006.01)
*A61B 17/88* (2006.01)

(52) U.S. Cl.
CPC .......... *A61B 17/8095* (2013.01); *A61B 17/70* (2013.01); *A61B 17/885* (2013.01)

(58) Field of Classification Search
CPC ..................................... A61F 2/44–2002/4495
See application file for complete search history.

(56) References Cited

U.S. PATENT DOCUMENTS

| 3,061,080 | A | 10/1962 | Stephen |
| 3,315,402 | A | 4/1967 | Scott et al. |
| 4,328,904 | A | 5/1982 | Iverson |
| 5,025,947 | A | 6/1991 | Leone |
| 5,259,501 | A | 11/1993 | Withers et al. |
| 5,342,365 | A | 8/1994 | Waldman |
| 5,676,990 | A | 10/1997 | Wawrzynski |
| 5,964,533 | A | 10/1999 | Ziglar |
| 5,989,289 | A * | 11/1999 | Coates ............... A61B 17/1671 623/17.16 |
| 6,010,502 | A | 1/2000 | Bagby |
| 6,350,283 | B1 * | 2/2002 | Michelson ............ A61F 2/4455 623/17.11 |
| 6,482,233 | B1 * | 11/2002 | Aebi ..................... A61F 2/4465 623/17.11 |
| 6,656,514 | B1 | 12/2003 | Tubbs |
| 6,830,570 | B1 * | 12/2004 | Frey ................... A61B 17/1604 623/17.16 |
| 7,591,388 | B2 | 9/2009 | Amormino |
| 7,618,454 | B2 * | 11/2009 | Bentley ................. A61F 2/4455 623/17.11 |
| 7,875,080 | B2 * | 1/2011 | Puno ................... A61F 2/30771 623/17.16 |
| 7,967,863 | B2 * | 6/2011 | Frey ................... A61B 17/1604 623/17.11 |
| 2001/0035414 | A1 | 11/2001 | Tyree |

(Continued)

*Primary Examiner* — Zade Coley

(57) ABSTRACT

A spinal implant comprises a body including a first vertebral engaging surface and a second vertebral engaging surface. At least one of the surfaces including a posterior linear side and an anterior arcuate side. Systems and methods of use are disclosed.

16 Claims, 3 Drawing Sheets

(56) References Cited

U.S. PATENT DOCUMENTS

| | | | |
|---|---|---|---|
| 2004/0220670 A1* | 11/2004 | Eisermann | A61B 17/1642 |
| | | | 623/17.14 |
| 2005/0143822 A1* | 6/2005 | Paul | A61F 2/4455 |
| | | | 623/17.16 |
| 2005/0252923 A1 | 11/2005 | Woolf | |
| 2005/0263523 A1 | 12/2005 | Moss | |
| 2007/0012701 A1 | 1/2007 | Amormino | |
| 2007/0233263 A1* | 10/2007 | Melkent | A61F 2/30771 |
| | | | 623/17.16 |
| 2008/0071372 A1* | 3/2008 | Butler | A61F 2/4465 |
| | | | 623/17.11 |
| 2009/0062917 A1* | 3/2009 | Foley | A61F 2/44 |
| | | | 623/17.16 |
| 2013/0110238 A1 | 5/2013 | Lindemann et al. | |

* cited by examiner

SPINAL IMPLANT SYSTEM AND METHOD

CROSS-REFERENCE TO RELATED APPLICATION

This application claims the benefits of U.S. Provisional Patent Application No. 62/047,966 filed Sep. 9, 2014, the contents of which being hereby incorporated in its entirety by reference.

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, interbody implants and spinal constructs can be delivered to a surgical site for fixation with bone to immobilize a joint. This disclosure describes an improvement over these prior art technologies.

SUMMARY

In one embodiment, a spinal implant comprises a body including a first vertebral engaging surface and a second vertebral engaging surface. At least one of the surfaces including a posterior linear side and an anterior arcuate side. In some embodiments, systems, surgical instruments and methods are provided.

BRIEF DESCRIPTION OF THE DRAWINGS

The present disclosure will become more readily apparent from the specific description accompanied by the following drawings, in which.

DETAILED DESCRIPTION

Figure 1:
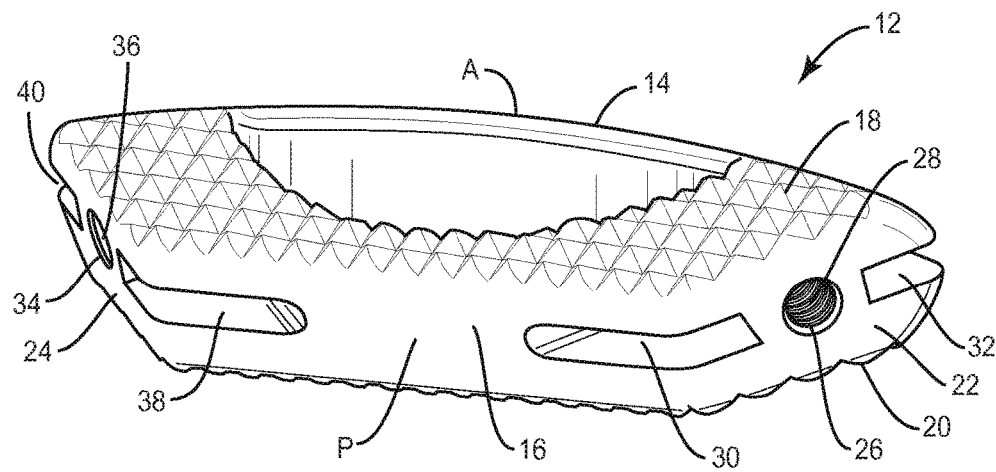
FIG. 1 is a perspective view of a component of one embodiment of a system in accordance with the principles of the present disclosure.
Figure 2:
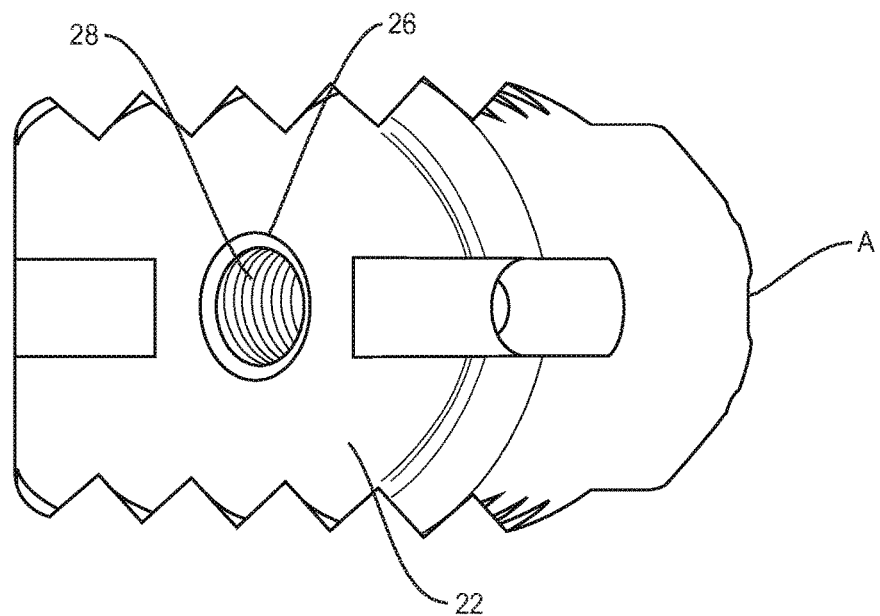
FIG. 2 is a side view of the component shown in FIG. 1.
Figure 3:
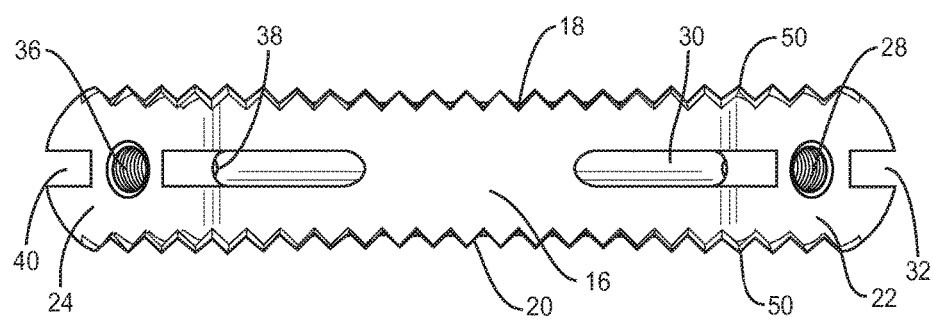
FIG. 3 is a side view of the component shown in FIG. 1.
Figure 4:
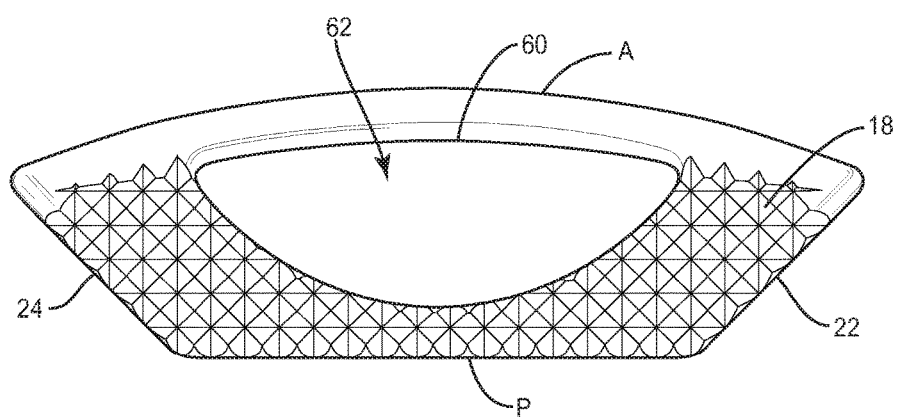
FIG. 4 is a side view of the component shown in FIG. 1.

The exemplary embodiments of the surgical system and related methods of use disclosed are discussed in terms of medical devices for the treatment of musculoskeletal disorders and more particularly, in terms of a surgical system including a spinal implant and a method for treating a spine. In one embodiment, the systems and methods of the present disclosure are employed with a spinal joint fusion, for example, with a cervical, thoracic, lumbar and/or sacral region of a spine. In one embodiment, the spinal implant includes an interbody device, a plate, spinal rods and/or bone fasteners.

In some embodiments, the present system comprises a spinal implant including at least one pedicle subtraction osteotomy (PSO) implant for use in creating and maintaining a more lordotic angle in a lumbar spine following removal of posterior bony structures of the spine.

In some embodiments, the present system comprises a spinal implant including a PSO implant having a bow-tie configuration. In some embodiments, the present system comprises a spinal implant designed for use during a PSO procedure. In some embodiments, the present system comprises a spinal implant including a stabilizing implant that provides a fixed fulcrum for restoring lordosis and height to an affected and/or selected vertebrae. In some embodiments, the present system comprises a spinal implant including a substantial bone graft pocket and can be inserted laterally, or through a posterior lumbar interbody fusion (PLIF), transforaminal lumbar interbody fusion (TILT) and anterior lumbar interbody fusion (ALIF) approaches. In some embodiments, the present system comprises a spinal implant that can be used with an inserter attached to either end, which may include a threaded hole and inserter prong notches on each lateral end for added control.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein. In one embodiment, a spinal implant, as described herein, may be formed substantially of a biocompatible metal, such as titanium and selectively coated with a bone-growth promoting material, such as HA. In one embodiment, a spinal implant, as described herein, may be formed substantially of a biocompatible polymer, such as PEEK, and selectively coated with a biocompatible metal, such as titanium, or a bone-growth promoting material, such as HA. In some embodiments, titanium may be plasma sprayed onto surfaces of the spinal implant to modify a radiographic signature of the spinal implant and/or improve bony ongrowth to the spinal implant by application of a porous or semi-porous coating of titanium.

Spinal implant system 10 may be employed, for example, with minimally invasive procedures, including percutaneous techniques, mini-open surgical techniques and/or open surgical techniques to deliver and introduce instrumentation and/or implants, such as, for example, an interbody implant, at a surgical site within a subject body of a patient, which includes, for example, a spine. In some embodiments, the implant can include spinal constructs including one or more bone fasteners, spinal rods, connectors and/or plates. In some embodiments, various components of spinal implant system 10 may be utilized in open or traditional spinal surgical techniques.

Figure 5:
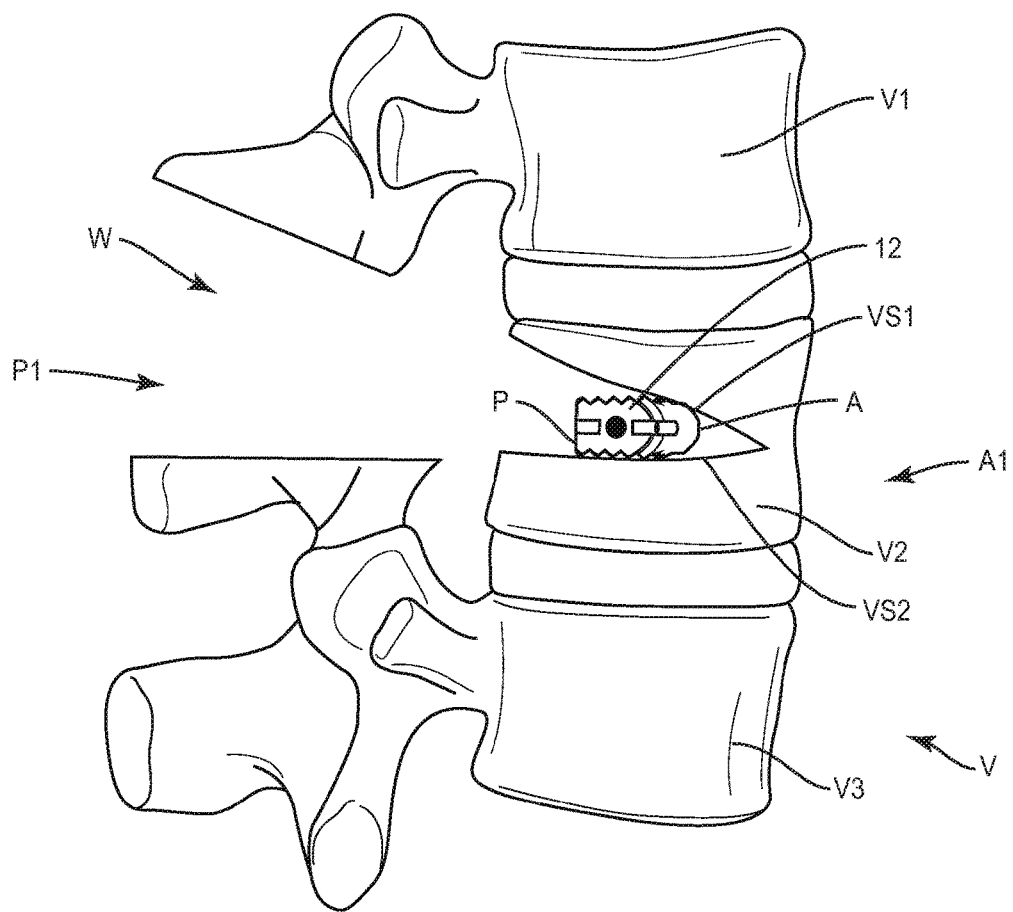
FIG. 5 is a side view of a component of one embodiment of a surgical system in accordance with the principles of the present disclosure disposed with vertebrae.

Spinal implant system 10 includes an interbody implant 12. Interbody implant 12 has an implant body that extends between an anterior surface 14 defining an anterior face A and a posterior surface 16 defining a posterior face P. In some embodiments, upon disposal of interbody implant 12 with vertebrae, anterior face A is oriented to face an anterior side of a body and be disposed adjacent an anterior portion of vertebrae, such as, for example, an anterior portion A1 of an intervertebral space of vertebrae V (FIG. 5). In some embodiments, upon disposal of interbody implant 12 with vertebrae, posterior face P is oriented to face a posterior side of the body and be disposed adjacent a posterior portion of vertebrae, such as, for example, a posterior portion P1 (FIG. 5). In some embodiments, interbody implant 12 is configured as a stabilizing implant that provides a fixed fulcrum for restoring lordosis and height to affected vertebrae.

Interbody implant 12 includes a vertebral engaging surface 18 and a vertebral engaging surface 20. Surfaces 18, 20 are each configured to engage tissue of a vertebral body. In some embodiments, surface 18 and/or surface 20 may be rough, textured, porous, semi-porous, dimpled, knurled, toothed, grooved and/or polished to facilitate engagement with tissue. In some embodiments, the vertebral tissue may include intervertebral tissue, endplate surfaces and/or cortical bone.

Surface 14 includes an arcuate configuration and surface 16 includes a linear configuration. Surface 14 is connected with surface 16 by lateral linear sides 22, 24. In some embodiments, sides, 22, 24 converge from surface 14 to surface 16 such that surface 14 has a greater dimension, such as, for example, spanned length than surface 16. In some embodiments, interbody implant 12 comprises a bow-tie configuration. In some embodiments, interbody implant 12 comprises one or more linear sides. In some embodiments, interbody implant 12 comprises one or more arcuate sides. In some embodiments, interbody implant 12 comprises a modified trapezoid configuration, which includes an arcuate side.

Side 22 includes a surface 26 that defines an opening 28 configured to receive a portion of a surgical instrument, such as, for example, an inserter, as described herein. In some embodiments, opening 28 includes a threaded surface. Surface 22 defines channels, such as, for example, notches 30, 32 configured to for engagement with prongs of the inserter. In one embodiment, notches 30, 32 are disposed on opposite sides of opening 28 such that notch 30 is disposed posteriorly and notch 32 is disposed anteriorly.

Side 24 includes a surface 34 that defines an opening 36 configured to receive a portion the inserter, as described herein. In some embodiments, opening 36 includes a threaded surface. Surface 34 defines channels, such as, for example, notches 38, 40 configured to for engagement with prongs of the inserter. In one embodiment, notches 38, 40 are disposed on opposite sides of opening 36 such that notch 38 is disposed posteriorly and notch 40 is disposed anteriorly. Providing notches 30, 32, 38, 40 and/or openings 28, 36 on each lateral side 22, 24 provides for added control of implant 12.

In some embodiments, surface 18 and/or surface 20 include tissue penetrating members, such as, for example, a plurality of teeth 50 disposed along surfaces 18, 20. In some embodiments, teeth 50 may have various configurations, for example, round, oval, rectangular, polygonal, irregular, tapered, offset, staggered, uniform and non-uniform.

Interbody implant 12 includes an inner surface 60 that defines an opening 62. Opening 62 is configured to receive an agent, which may include bone graft (not shown) and/or other materials, as described herein, for employment in a fixation or fusion treatment. In some embodiments, the agent is packed into opening 62 after interbody implant 12 is disposed with vertebrae. In some embodiments, the cross-sectional geometry of opening 62 may have various configurations, such as, for example, hexagonal, round, oval, oblong, triangular, polygonal having planar or arcuate side portions, irregular, uniform, non-uniform, consistent, variable, horseshoe shape, U-shape or kidney bean shape.

In assembly, operation and use, spinal implant system 10, similar to the systems and methods described herein, is employed during a surgical procedure, such as, for example, a PSO, a vertebral column resection (VCR) or other correction treatment to treat, for example, scoliosis and/or kyphosis of a spine. In some embodiments, one or all of the components of spinal implant system 10 can be delivered or implanted as a pre-assembled device or can be assembled in-situ. In some embodiments, one or all of the components of spinal implant system 10 may be completely or partially revised, removed or replaced.

To treat an affected section of vertebrae V, as shown in FIG. 5, a medical practitioner obtains access to a surgical site including vertebra V1, V2, V3. In some embodiments, spinal implant system 10 can be used in any existing surgical method or technique including open surgery, mini-open surgery, minimally invasive surgery and percutaneous surgical implantation, whereby a section of vertebrae V including vertebra V1-V3 are accessed through a mini-incision, or sleeve that provides a protected passageway to the area. Once access to the surgical site is obtained, the particular surgical procedure can be performed for treating the spine disorder. In some embodiments, posterior bony structure is removed from vertebrae V. In some embodiments, posterior bony structure, such as, for example, pedicle tissue is removed as part of a PSO procedure. In some embodiments, spinal implant system 10 is employed with a Grade 3 PSO procedure. In some embodiments, spinal implant system 10 is employed with a Grade 4 PSO procedure.

An incision is made in the body of a patient and a cutting instrument (not shown) creates a surgical pathway for implantation of components of spinal implant system 10. A preparation instrument (not shown) can be employed to prepare tissue surfaces VS1, VS2 of vertebrae V, as well as for aspiration and irrigation of a surgical region. In some embodiments, a wedge W portion of bone and/or other tissue is removed from a selected vertebral level including, for example, vertebra V2 and posterior portions of the spine, such as, for example, pedicles, laminae and/or spinous process, and adjacent intervertebral disc tissue remains intact, as shown in FIG. 5. In some embodiments, a portion of a selected vertebra and intervertebral disc tissue disposed between vertebrae can be removed to define a vertebral space and adjacent vertebra remain intact. In some embodiments, the vertebral space can include posterior portions of the spine, such as, for example, pedicles, laminae and/or spinous process.

In some embodiments, pilot holes are made in selected vertebra of vertebrae V for receiving fixation elements, such as, for example, bone fasteners. Each of the bone fasteners is inserted or otherwise engaged with a particular vertebra. In some embodiments, spinal constructs and rods are employed as provisional and/or working rods to support vertebrae V during a corrective procedure. In some embodiments, spinal implant system 10 may include one or a plurality of the spinal constructs. In some embodiments, the plurality of spinal constructs may be disposed in various alternate orientations, such as, for example, side by side, parallel, transverse and/or other angular orientations such as acute or obtuse, co-axial and/or may be offset or staggered. In some embodiments, the plurality of spinal constructs may provide a template configuration for permanently implantable spinal rods, such as, implantable, final, permanent, removable, non-removable, bio-absorbable, resorbable and/or bio-degradable, and/or comprise permanently implantable spinal rods.

An inserter is connected with lateral side 22 and/or or lateral side 24. The inserter delivers interbody implant 12 through the incision along the surgical pathway adjacent to the surgical site for implantation with wedge W. Anterior surface A faces an anterior side of the body adjacent anterior portion A1 and posterior surface P faces a posterior side P1 of the body, as described herein.

The inserter delivers interbody implant 12 into wedge W between vertebral surfaces VS1, VS2. Interbody implant 12 is disposed with wedge W such that surface 18 is disposed in a cephalad orientation of the body and surface 20 is disposed in a caudal orientation of the body. As interbody implant 12 is inserted into wedge W, teeth 50 translate along vertebral surfaces VS1, VS2 for engagement of surfaces 18, 20 with the soft tissues, bone and/or fluids of vertebral surfaces VS1, VS2.

Vertebrae V is derotated, aligned, corrected and/or treated via manipulation in connection with the PSO procedure. Surfaces 18, 20 engage vertebral surfaces VS1, VS2 in connection with the orientation of manipulated vertebrae V to provide a fixed fulcrum configuration therebetween and a stabilizing construct that restores lordosis and height to vertebrae V including affected vertebral levels V1-V3.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiopaque markers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of plates, connectors and/or bone fasteners for use with a single vertebral level or a plurality of vertebral levels.

In one embodiment, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

In some embodiments, the components of spinal implant system 10 may be employed to treat progressive idiopathic scoliosis with or without sagittal deformity in either infantile or juvenile patients, including but not limited to pre-pubescent children, adolescents from 10-12 years old with continued growth potential, and/or older children whose growth spurt is late or who otherwise retain growth potential. In some embodiments, the components of spinal implant system 10 and related methods of use may be employed to prevent or minimize curve progression in individuals of various ages.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a body including a first vertebral engaging surface and a second vertebral engaging surface, at least one of the surfaces including a posterior linear side that is linear from a first end of the posterior linear side to an opposite second end of the posterior linear side and an anterior arcuate side that is continuously curved from a first end of the anterior arcuate side to an opposite second end of the anterior arcuate side, at least one of the surfaces including a first linear side that connects the first ends and a second linear side that connects the second ends,
wherein the body includes first and second notches and a threaded opening positioned between the notches, the first notch extending into the first linear side and the posterior linear side, the second notch extending into the first linear side and the anterior arcuate side.

2. A spinal implant as recited in claim 1, wherein each of the surfaces include a posterior linear side and an anterior arcuate side.

3. A spinal implant as recited in claim 1, wherein the first linear side is linear from the first end of the posterior linear side to the first end of the anterior arcuate side and the second linear side is linear from the second end of the posterior linear side to the second end of the anterior arcuate side.

4. A spinal implant as recited in claim 1, wherein each of the surfaces include the posterior linear side, the anterior arcuate side, the first linear side and the second linear side.

5. A spinal implant as recited in claim 1, wherein the body comprises a fixed fulcrum disposed between vertebral engaging surfaces.

6. A spinal implant as recited in claim 1, wherein the anterior arcuate side spans a greater length than the posterior linear side.

7. A spinal implant as recited in claim 1, wherein the linear sides each include a threaded opening configured for engagement with a surgical inserter.

8. A spinal implant as recited in claim 1, wherein the first and second linear sides each include a threaded opening and at least one notch disposed adjacent the opening, the opening and the notch being configured for engagement with a surgical inserter.

9. A spinal implant as recited in claim 1, wherein the first linear side includes a first threaded lateral opening and a pair of notches disposed adjacent the first opening and the second linear side includes a second threaded lateral opening and a pair of notches disposed adjacent the second opening.

10. A spinal implant as recited in claim 1, wherein the body includes an opening that extends through the surfaces, the opening being configured for disposal of an agent.

11. A spinal implant as recited in claim 1, wherein the body includes third and fourth notches and a second threaded opening positioned between the third and fourth notches, the third notch extending into the second linear side and the posterior linear side, the fourth notch extending into the second linear side and the anterior arcuate side.

12. A spinal implant comprising:
a body including a first vertebral engaging surface and a second vertebral engaging surface, the body including a posterior wall extending between the surfaces that is linear from a first end of the posterior wall to an opposite second end of the posterior wall, the body including an anterior wall extending between the surfaces that is continuously curved from a first end of the anterior wall to an opposite second end of the anterior wall, the body including a first wall that connects the first ends and a second wall that connects the second ends,
wherein the body includes first and second notches and a threaded opening positioned between the notches, the first notch extending into the first wall and the posterior wall, the second notch extending into the first wall and the anterior wall.

13. A spinal implant as recited in claim 12, wherein the first wall is linear from the first end of the posterior wall to the first end of the anterior wall and the second wall is linear from the second end of the posterior wall to the second end of the anterior wall.

14. A spinal implant as recited in claim 12, wherein the first wall includes a first threaded lateral opening and a pair of notches disposed adjacent the first opening and the second wall includes a second threaded lateral opening and a pair of notches disposed adjacent the second opening.

15. A spinal implant as recited in claim 12, wherein the body includes third and fourth notches and a second threaded opening positioned between the third and fourth notches, the third notch extending into the second wall and the posterior wall, the fourth notch extending into the second wall and the anterior wall.

16. A spinal implant comprising:
a body including a first vertebral engaging surface and a second vertebral engaging surface, the body including a posterior wall extending between the surfaces that is linear from a first end of the posterior wall to an opposite second end of the posterior wall, the body including an anterior wall extending between the surfaces that is continuously curved from a first end of the anterior wall to an opposite second end of the anterior wall, the body including a first wall that connects the first ends and a second wall that connects the second ends,
wherein the first wall is linear from the first end of the posterior wall to the first end of the anterior wall and the second wall is linear from the second end of the posterior wall to the second end of the anterior wall,
wherein the body includes first and second notches and a threaded opening positioned between the notches, the first notch extending into the first wall and the posterior wall, the second notch extending into the first wall and the anterior wall, and
wherein the body includes third and fourth notches and a second threaded opening positioned between the third and fourth notches, the third notch extending into the second wall and the posterior wall, the fourth notch extending into the second wall and the anterior wall.

* * * * *